United States Patent
Neuvonen et al.

(10) Patent No.: US 10,300,294 B2
(45) Date of Patent: May 28, 2019

(54) BI-PHASIC PAIRED PULSE TRANSCRANIAL MAGNETIC STIMULATION

(75) Inventors: Tuomas Neuvonen, Espoo (FI); Henri Hannula, Helsinki (FI); Gustaf Jarnefelt, Helsinki (FI); Jarmo Laine, Helsinki (FI)

(73) Assignee: Nexstim Oyj, Helsinki (FI)

( * ) Notice: Subject to any disclaimer, the term of this patent is extended or adjusted under 35 U.S.C. 154(b) by 0 days.

(21) Appl. No.: 13/824,419

(22) PCT Filed: Sep. 7, 2012

(86) PCT No.: PCT/FI2012/050875
§ 371 (c)(1),
(2), (4) Date: Aug. 30, 2013

(87) PCT Pub. No.: WO2013/132136
PCT Pub. Date: Sep. 12, 2013

(65) Prior Publication Data
US 2015/0018692 A1 Jan. 15, 2015

Related U.S. Application Data

(60) Provisional application No. 61/606,687, filed on Mar. 5, 2012.

(51) Int. Cl.
*A61N 2/00* (2006.01)
*A61N 2/02* (2006.01)
(Continued)

(52) U.S. Cl.
CPC ............ *A61N 2/02* (2013.01); *A61B 5/0077* (2013.01); *A61B 5/0484* (2013.01); *A61N 2/008* (2013.01); *A61B 5/0476* (2013.01)

(58) Field of Classification Search
CPC .......... A61N 2/00; A61N 2/002; A61N 2/004; A61N 2/006; A61N 2/008; A61N 2/02; A61N 1/40
See application file for complete search history.

(56) References Cited

U.S. PATENT DOCUMENTS 5,885,976 A * 3/1999 Sandyk .................... 514/159
6,117,066 A 9/2000 Abrams
(Continued)

FOREIGN PATENT DOCUMENTS

CN 1404793 A 3/2003
EP 0788813 A1 2/1997
(Continued)

OTHER PUBLICATIONS

Albert G C et al: "Deep brain stimulation, vagal nerve stimulation and transcranial stimulation: An overview of stimulation parameters and neurotransmitter release", Neuroscience and Biobehavioral Reviews, Pergamon Press LTD, XX, vol. 33, No. 7, Jul. 1, 2009.

*Primary Examiner* — Carrie R Dorna
(74) *Attorney, Agent, or Firm* — Seppo Laine Oy

(57) ABSTRACT

It is an aspect of the present invention to provide a method for recording a response to Transcranial Magnetic Stimulation (TMS) utilizing a bi-phasic double pulse pair from a TMS coil device to stimulate a subject wherein the second pulse has a lower amplitude compared to the first pulse in the bi-phasic double pulse pair. Significant advantages are achieved using bi-phasic double pulse pairs, particularly where the second pulse in a pair has an intensity lower than the first. Obtaining measurements is simpler and more accurate as the number and intensity of stimulation can be reduced compared to standard single pulse stimulation.

15 Claims, 3 Drawing Sheets

(51) Int. Cl.
 *A61B 5/00* (2006.01)
 *A61B 5/0484* (2006.01)
 *A61B 5/0476* (2006.01)

(56) References Cited

U.S. PATENT DOCUMENTS

| | | | | |
|---|---|---|---|---|
| 2006/0015153 A1* | 1/2006 | Gliner | ............ | A61N 1/3606 |
| | | | | 607/45 |
| 2007/0142874 A1* | 6/2007 | John | ............ | 607/45 |
| 2007/0293916 A1* | 12/2007 | Peterchev | ............ | A61N 2/006 |
| | | | | 607/61 |
| 2009/0099405 A1* | 4/2009 | Schneider | ............ | A61N 2/02 |
| | | | | 600/13 |
| 2011/0152967 A1 | 6/2011 | Simon et al. | | |

FOREIGN PATENT DOCUMENTS

| | | |
|---|---|---|
| WO | WO 2006019764 A2 | 2/2006 |
| WO | WO 2006134598 A2 | 12/2006 |
| WO | WO 2010146220 A1 | 12/2010 |

* cited by examiner

BI-PHASIC PAIRED PULSE TRANSCRANIAL MAGNETIC STIMULATION

FIELD OF INVENTION

The present invention relates to Transcranial Magnetic Stimulation (TMS) using paired pulses.

BACKGROUND OF THE INVENTION

TMS has a variety of uses in the field of medicine and research. Typically, a TMS coil device is used to stimulate a subject's brain non-invasively. The TMS coil in typical operation produces a series of single pulses which stimulate a particular location on or within a subject's brain.

In most non-therapy situations it is important to measure a response from the subject based on the stimulation received. This is particularly important when it comes to mapping brain functions.

A problem exists with the current single pulse stimulation method as a subject's response to the stimulation may begin during subsequent stimulations in a single series of pulses. As many measurement devices are also affected by the stimulation of the coil readings and measurements are either impossible or unreliable during the actual stimulation.

Therefore, there exists a need to reduce the amount of stimulation needed to give to a subject in order to elicit a response, normally described as the motor threshold (MT). The options for limiting the amount of stimulation given, in number of pulses and intensity, is limited using single pulses while still achieving a measureable response from the subject to the stimulation.

SUMMARY OF THE INVENTION

It is the object of the present invention to provide a method of utilizing bi-phasic double pulses in Transcranial Magnetic Stimulation.

It is an aspect of the present invention to provide a method for recording a response to Transcranial Magnetic Stimulation (TMS) utilizing a bi-phasic double pulse pair from a TMS coil device to stimulate a subject wherein the second pulse has a lower amplitude compared to the first pulse in the bi-phasic double pulse pair, and measuring the subject's response to the TMS stimulation after said TMS stimulation.

Furthermore, it is an aspect of certain embodiments of the present invention to provide a method wherein the measuring step takes place at a point in time when the TMS coil device is not actively producing magnetic stimulation.

According to certain embodiments the second pulse of the bi-phasic double pulse pair is generated less than 1 ms, preferably less than 0.5 ms after said first pulse of the bi-phasic double pulse pair has completed. Additionally, there may be no magnetic stimulation generated by the TMS coil device within 2 ms, preferably within 15 ms, more preferably within 50 ms, still more preferably within 100 ms of the conclusion of the second pulse of the bi-phasic double pulse pair.

Furthermore, according to certain embodiments no magnetic field is generated by the TMS coil device between the conclusion of the second pulse of the bi-phasic double pulse pair and prior to the measurement of at least a first portion of the subject's response to said bi-phasic double pulse pair.

According to certain embodiments the second pulse of the bi-phasic double pulse pair is between 5-50%, preferably between 10-20% lower than the first pulse of the bi-phasic double pulse pair. Additionally, the amplitude of the first pulse of the bi-phasic double pulse pair is 5-40%, preferably between 15-30%, more preferably between 18-20% lower than the normal motor threshold for the subject.

Furthermore, it is an aspect of the present invention to provide a non-transitory computer readable medium having stored thereon a set of instruction for causing a processor to control a TMS coil device and a measuring device to carry out the steps the methods described herein.

DETAILED DESCRIPTION OF EXAMPLE EMBODIMENTS

Paired pulses, also called double pulses or high frequency bursts, can be used in order to increase a subject's physiological response to a stimulus or to more effectively interrupt an ongoing cognitive brain processes. In general, the intensity of the first and later pulse(s) of a pair of pulses or burst of pulses can be equal, substantially equal, or the first pulse can have a higher or lower intensity than a second or later pulse(s). However, as will be discussed herein, significant advantages are achieved when the second or subsequent pulse has a lower amplitude compared to the first in a pair or series of pulses.

Bi-phasic double pulse stimulation can be used in place of a train of repetitive transcranial magnetic stimulation pulses. A bi-phasic double pulse comprises, or consists, of two full sinus waves. Once the first bi-phasic sinus wave pulse is delivered through the stimulation coil then there is delivered a second, bi-phasic sinus wave pulse. This can be accomplished by discharging two separate capacitors at controlled intervals. Additionally, the arrangement may include a monophasic stimulator circuit.

Figure 1:
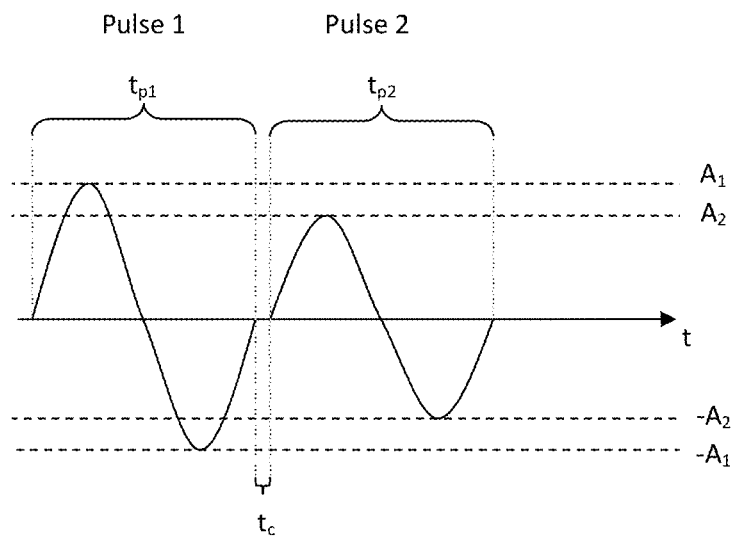
FIG. 1 shows an example of a system according to an embodiment of the present invention.
Figure 2:
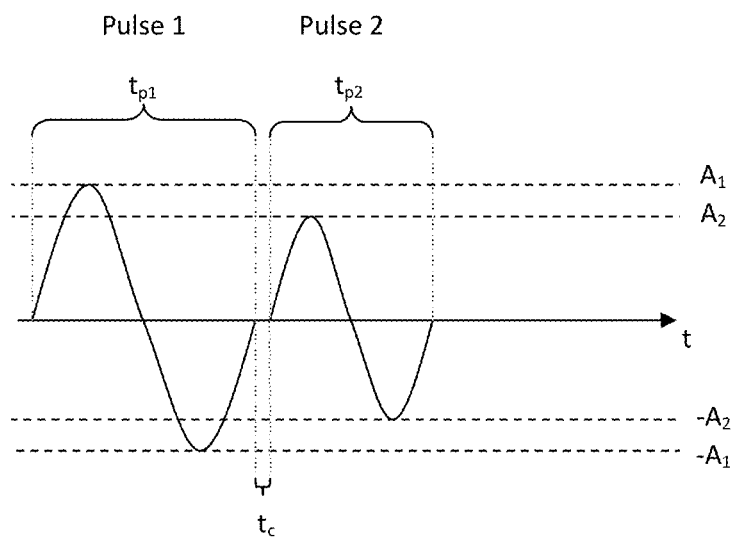
FIG. 2 shows another example of a system according to an embodiment of the present invention.

FIGS. 1 and 2 are illustrative of the present concept. Pulse 1 has an amplitude of $A_1$, and a period of $t_{p1}$. Similarly, pulse 2 has an amplitude of $A_2$, and a period of $t_{p2}$. The time between the first and second pulses of the bi-phasic double pulse pair, consisting of pulse 1 and pulse 2, is $t_c$.

The interpulse interval $t_c$ for double pulses is often selected based on expected physiological effects. Typically, short pulse repetition intervals have opposite effects from long repetition intervals. For example, double pulses used in transcranial magnetic stimulation can have can interpulse intervals ranging from, for instance, 1-20 milliseconds, corresponding to repetition frequency of 50 Hz-1000 Hz.

Due to constraints of current technology, there is a short pause in stimulation between the two pulses of a bi-phasic double pulse pair. The pause is caused in part by the necessity of the first pulse to return through the coil. One constraint on the length of the pause is the speed of any switcher(s) used in the TMS device and/or coil. Other constraints are the amount of energy lost from a previous pulse and the amount of time necessary for recharging a capacitor between pulses. The length of the pause is between, for example, 0.1-15 ms. This pause can be reduced or negated as much as physically possible at least in part with the construction of a TMS device with the necessary capacitor or set of capacitors and switcher(s) to release a second biphasic pulse after a first without the need of recharging or of recharging only slightly between pulses. Additionally, a pause having a similar duration, for example 0.1-15 ms, may be designed in to the bi-phasic double pulse if so desired by the operator.

As is shown in FIGS. 1 and 2, the period of the second pulse may be the same as the first pulse or it may be different. In the representative case of FIG. 2, the period of the second pulse is shorter than the period of the first pulse. According to certain embodiments the period of the second pulse may also be greater than that of the first pulse.

During stimulation using bi-phasic double pulses it is beneficial to begin each pulse at 0, or in a neutral, i.e. not in the positive or negative phase, which is shown in each of FIGS. 1-5. Examples of the total duration between peak amplitudes of a first and second pulse from a bi-phasic double pulse are 3, 7 and 15 ms. Additionally, examples of the difference between the peak amplitudes of the first and second pulses range from the second pulse being between 5-50% weaker than the first pulse. However, these parameters are merely beneficial and some modification thereof by one of ordinary skill in the art falls within the scope of the present application.

In general, the amplitude of the first pulse can be determined and modified as described above with regards to other means of pulse stimulation. For example, when using bi-phasic double pulses the motor threshold (MT) is determined and used as a baseline, and/or guide in determining initial stimulation levels for operations like cognitive mapping. One of the benefits of using bi-phasic double pulses is that the amplitude of the first pulse in a bi-phasic double pulse can be between, for example, 15-30% less than the amplitude of one or more mono-phasic pulses or standard repetitive TMS to elicit the same or greater response for the subject. In some cases, when a subject's mono-phasic stimulation MT is determined, utilizing a bi-phasic double pulse stimulation having the first amplitude of 18-20% less than the subject's mono-phasic stimulation MT can elicit responses up to 10 times greater than expected.

Several benefits arise from using bi-phasic double pulses. For example, because the absolute amplitude of the pulses from a bi-phasic double pulse can be less than that required by a similar mono-phasic, or series of mono-phasic pulses, the total exposure for the subject and operator can be limited. Similarly, the reduction of peak amplitude can reduce the temperature increase on cells in the brain. Another example is that the reduced peak amplitude can lessen negative effects of stimulation on surface muscles and the scalp. Furthermore, as the effects of a bi-phasic pulse can be, for example, up to or even greater than 10 times that of a mono-phasic pulse stimulation.

Figure 3:
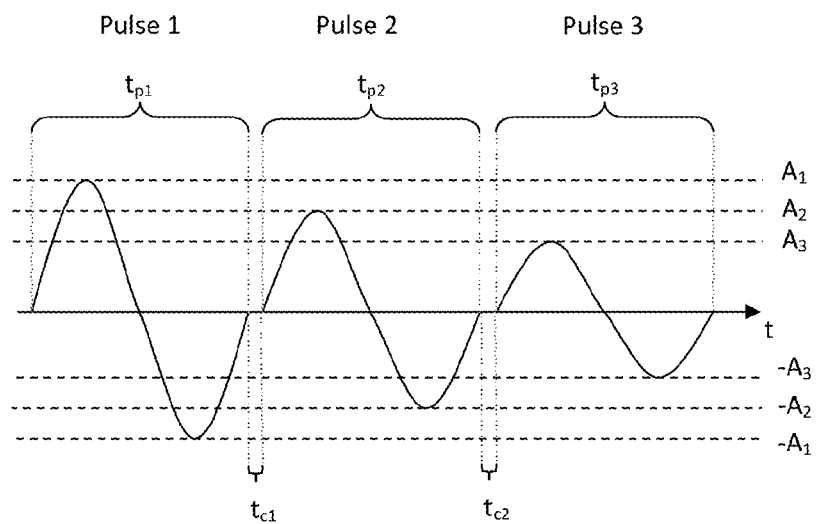
FIG. 3 shows another example of a system according to an embodiment of the present invention which includes a separate cognitive package.
Figure 4:
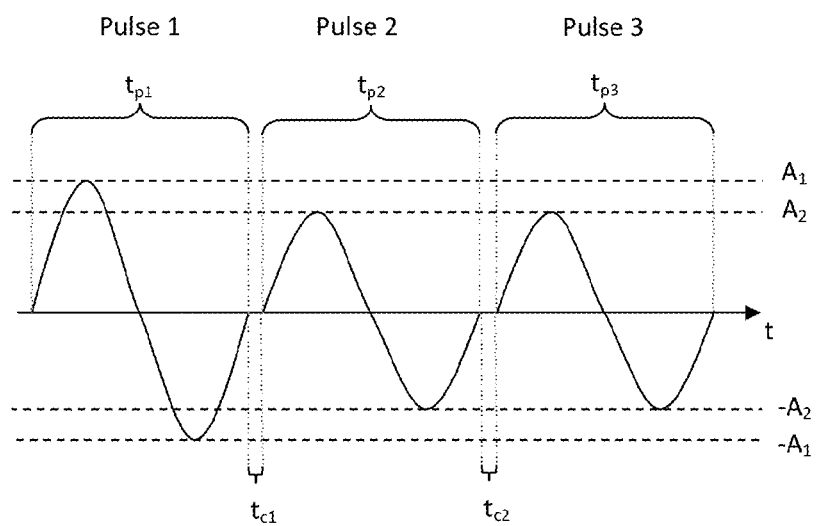
FIG. 4 shows three pulses wherein the third pulse is equal to a second pulse according to an embodiment of the present invention.
Figure 5:
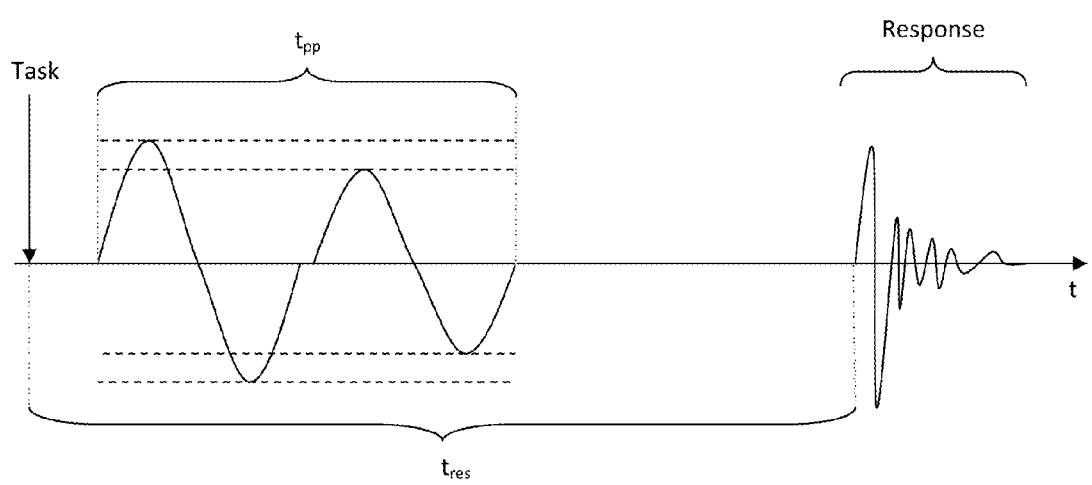
FIG. 5 shows two pulses followed by a response according to an embodiment of the present invention.

According to certain embodiments of the present invention, in addition to bi-phasic double pulse pairs, an additional pulse, having an amplitude of $A_3$, and a period of $t_{p3}$ may be added after the second pulse to form a high frequency burst. The interval between the second and third pulses, as shown in FIGS. 3 and 4 is denoted as $t_{c2}$.

The amplitude of a third pulse is less than that of the amplitude of the first pulse. However, the amplitude of the third pulse may be equal to that of the second pulse, as shown for example in FIG. 4, or it may be lesser than that of the second pulse, as shown for example in FIG. 5. Similar to the discussion above, the period of the third pulse may be greater than, less than or equal to that of the first and/or second pulse.

A major benefit to the present invention is that the absolute number of pulses during a single stimulation can be decreased. A primary result of this is that more locations can be stimulated during a single session while keeping the total amount of stimulation to the subject the same. However, another result of a reduced number of pulses during a single stimulation is that it is possible to measure the subject's, i.e. the subject receiving stimulation, actual response to the first and/or second stimulations more effectively and accurately.

Many measurement devices, for example such as EEG's, microphones and video recording devices, can be effected by the magnetic fields generated by TMS coil devices. As such, if a measurement device is actively trying to measure a subject's response and is active while the TMS coil device is still stimulating the subject then the results can be affected and a true reading hard to obtain. Furthermore, in normal repetitive TMS there is a likelihood that during a long series of pulses that the coil will move slightly during the stimulation. In such an instance it is practically impossible for a measuring device to determine which stimulation, at which exact location, is responsible for a detected response of a subject out of a long series of stimulations.

Therefore, according to certain embodiments the measurement of the response does not commence prior to the end of the second, or tertiary, pulse. Furthermore, according to certain embodiments the measurement device is turned off prior to the commencement of the first pulse. In such cases the measurement device is then turned on at a time after the second or tertiary pulse ends. In such a context, turned off and turned on can mean actually turning on or off the measurement device or it may be turning on/off a function or functions of the measurement device, such as, for example active detection and/or recording of measurements.

Additionally, the measurement of a response for a certain bi-phasic double pulse pair takes place prior to the start of a subsequent stimulation, i.e. the measurement takes place when there is no induced stimulation by the TMS coil device.

When discussing the measurement of a response to stimulation it is important to note that the full response of a subject, for example in the case of an EEG, may take a relatively long time. However, the initial portion of the response, or non-response, is typically sufficient to determine that the stimulation did or did not have the desired effect on the subject. Therefore, according to certain examples it is only necessary that there is no stimulation during the time necessary to measure the initial portion of the subject's response.

A particularly advantageous use of the present invention deals with cognitive brain mapping. During cognitive brain mapping a subject is given a task, such as to answer a question or name an object. During or after presentation of the task the subject is subjected to some stimulation at a particular location to determine if that location affects the particular cognitive function. A problem which is encountered in such situations is that TMS coil devices generate a large amount of noise during stimulation. In order to accurately measure a subjects response it is desirable to use some type of audio recording as a measurement device of the subject's response. Microphones can be sensitive to magnetic stimulation and can also have difficulty determining the onset of a subject's speech while a TMS coil is in the process of producing a stimulation.

By using a bi-phasic double pulse pair in place of, for example, a series of standard repetitive TMS stimulations it is possible to allow more time between the end of stimulation and the onset of the subjects speech so that speech can be detected without the noise of stimulation. This can insure little or no overlap between the subject's speech and stimulation, making the detection of speech onset much easier and more reliable. Furthermore, another benefit can be that the greater response elicited by bi-phase double pulses can add a higher degree of reliability to cognitive results, e.g. reduce false negative results.

The use of paired pulses and/or high frequency bursts allow for easier detection of effects from stimulation. One or more of said paired pulses or high frequency bursts can be used in a single set of stimulation pulses as described above with respect to the typical stimulation parameters. Therefore, through their use, an operator can more easily determine if a stimulated region has a speech function.

Furthermore, several embodiments of the present invention may be described as follows. A method of inducing a bi-phasic double pulse from a Transcranial Magnetic Stimulation (TMS) coil device comprising the steps of; releasing a first amount of current from a capacitor, said first amount of current being capable of generating a first bi-phase stimulation wave having a first amplitude, and releasing a second amount of current from a capacitor, said second amount of current being capable of generating a second bi-phase stimulation wave having a second amplitude.

According to such methods, the second amount of current is released after said first amount of current. Additionally, the second amount of current is released after said first amount of current has traveled through an induction coil portion of said TMS coil device.

Such methods may further comprise the step of activating a switch to allow the second amount of current through an induction coil portion of said TMS coil device at a time after said first amount of current has traveled through said induction coil portion. Additionally, said releasing of the second amount of current occurs at or before the activation of said switch.

The second amount of current can be released from the same capacitor as the first amount of current. However, the second amount of current is released from a different capacitor as the first amount of current. In either instance, the method may further comprise the step of at least partially recharging the capacitor from which the first amount of current is released. For instance, the method may further comprise the step of at least partially recharging the capacitor from which the first amount of current is released prior to the release of the second amount of current.

According to such methods the second bi-phase wave stimulation can be generated less than 1 ms, preferably less than 0.5 ms after said first bi-phase wave stimulation is completed. Furthermore, the second bi-phase wave stimulation may be generated between 0.1-15 ms, preferably between 0.1-5 ms, more preferably between 0.1-1 ms after said first bi-phase wave stimulation is completed.

Furthermore, according to such methods the first amount of current can be a combination of currents released from more than one capacitor. Similarly, the second amount of current can be a combination of currents released from more than one capacitor.

According to certain such embodiments there is no stimulation generated by an induction coil portion of the TMS coil device within 2 ms, preferably within 15 ms, more preferably within 50 ms, still more preferably within 100 ms of the conclusion of stimulation from the second amount of current.

Furthermore, according to certain such embodiments the method comprises a further step of activating a switch to prevent stimulation once the second amount of current has passed through an induction portion of said TMS coil device.

EXAMPLES

Several examples were carried according to aspects of the present invention which demonstrate the unexpected results associated with the present invention.

First, motor mapping using single pulses was carried out. The abductor pollicis brevis (APB) 'hotspot' and moter threshold (MT) were determined on both hemispheres. The tibialis anterior (TA) 'hotspot' and MT on one hemisphere (left in the present examples) was also determined. 20 responses at each APB and TA location were measured using 110% MT. As such, during this phase each subject was submitted to approximately 200 pulses in total.

Second, using the 110% MT determined in the first step a 3 ms inter-stimulation interval (ISI) paired pulse paradigm was utilized. 20 pulses on each APB and on the single TA were given to the subject. Then the MT was determined at each location. In total, during this step approximately 100-150 paired pulse stimulations were given.

The second portion of the test was then repeated twice, first using a 7 ms ISI paired pulse paradigm followed by a 15 ms IS paired pulse paradigm.

The MT determined in each of the secondary steps was compared to the single pulse MT. Additionally, the MEP amplitude and latency was determined for each method, using the 20 pulse average.

The pulse intensity of the second pulse was 90% of that of the first pulse and the inter-trail interval was 5 s. The first phase required 20-30 minutes, and each secondary phase required approximately 10 minutes.

Some of the results are shown below.

Subject A

| muscle | single-pulse | paired-pulse 3 ms | paired-pulse 7 ms | paired-pulse 15 ms |
| --- | --- | --- | --- | --- |
| APB, right MT | 29% | 29% | 29% | 31% |
| APB, left MT | 32% | 32% | 33% | 32% |
| TA, right MT | 62% | 53% | 61% | 64% |

Subject B

| muscle | single-pulse | paired-pulse 3 ms | paired-pulse 7 ms | paired-pulse 15 ms |
| --- | --- | --- | --- | --- |
| APB, right MT | 41% | 36% | 39% | 42% |
| APB, left MT | 43% | 43% | 44% | 41% |
| TA, right MT | 89% | 78% | 77% | 87% |

Subject C

| muscle | single-pulse | paired-pulse 3 ms | paired-pulse 7 ms | paired-pulse 15 ms |
|---|---|---|---|---|
| APB, right MT | 53% | 47% | 52% | 53% |
| APB, left MT | 43% | 39% | 42% | 43% |
| TA, right MT | 80% | 64% | 67% | 70% |

As can be seen from the results above, the MT for at least one region and at least one paired pulse paradigm for each subject was significantly reduced compared to the single-pulse stimulation. As each subjects cranial anatomy differs there are more effective paradigms for certain subjects. Therefore, it can simply be determined prior to mapping or therapy which paired pulse paradigm, either selected from the three above or others as described herein, is best suited for the area of the particular subjects brain.

All of the methods described herein can be implemented, for instance, by a system including a control means arranged to carry out or regulate said steps. An example of a control means capable of carrying out said function would be a processor coupled to a non-transitory computer readable medium having stored thereon a set of instructions for causing the processor to perform and/or regulate the method steps disclosed herein.

The examples and embodiments disclosed herein are illustrative of the concept of the present invention. Those of ordinary skill in the art will recognize variations and additional uses for the present invention which while not explicitly disclosed herein none the less do not depart from the scope of the present invention.

The invention claimed is:

1. A method of recording a response to Transcranial Magnetic Stimulation (TMS) comprising the steps of:
   inducing a bi-phasic double pulse pair from a single stimulation coil of a TMS coil device to stimulate a subject wherein the second bi-phasic pulse of the bi-phasic double pulse pair has a lower amplitude compared to the first bi-phasic pulse in the bi-phasic double pulse pair, and
   measuring the subject's response to the bi-phasic double pulse pair,
   wherein no magnetic field is generated by the TMS coil device between the conclusion of the second bi-phasic pulse of the bi-phasic double pulse pair and prior to the measurement of at least a first portion of the subject's response to said bi-phasic double pulse pair.

2. A method in accordance with claim 1, wherein said measuring step takes place at a point in time when the TMS coil device is not actively producing magnetic stimulation.

3. A method according to claim 1, wherein said second bi-phasic pulse of the bi-phasic double pulse pair is generated less than 1 ms after said first bi-phasic pulse of the bi-phasic double pulse pair has completed.

4. A method according to claim 1, wherein there is no magnetic stimulation generated by the TMS coil device within 2 ms of the conclusion of the second bi-phasic pulse of the bi-phasic double pulse pair.

5. A method according to claim 1, wherein the at least first portion of the subject's response is sufficient to determine an effect of the stimulation on the subject.

6. A method according to claim 1, wherein the measuring step is carried out by an EEG, microphone, video recorder or combination thereof.

7. A method according to claim 1, further comprising activating a measuring device for measuring the subject's response once the second bi-phasic pulse of the bi-phasic double pulse pair has completed.

8. A method according to claim 1, further comprising deactivating a measuring device for measuring the subject's response prior to the first bi-phasic pulse of the bi-phasic double pulse pair.

9. A method according to claim 1, wherein a task is presented to the subject prior to the first bi-phasic pulse of the bi-phasic double pulse pair and measuring the response of the subject includes determining their response to the task.

10. A method according to claim 1, wherein the amplitude of the second bi-phasic pulse of the bi-phasic double pulse pair is between 5-50% lower than the amplitude of the first bi-phasic pulse of the bi-phasic double pulse pair.

11. A method according to claim 1, wherein the amplitude of the first bi-phasic pulse of the bi-phasic double pulse pair is 5-40% lower than the normal motor threshold for the subject.

12. A method according to claim 1, wherein the bi-phasic double pulses are discharged from a single capacitor.

13. A method according to claim 1, wherein the bi-phasic pulses are discharged from a single capacitor and wherein a stimulator circuit connected to the TMS coil device is capable of discharging the second bi-phasic pulse within 0.5-100 ms from the first bi-phasic pulse.

14. A method according to claim 1 wherein the amplitude of the first bi-phasic pulse of the bi-phasic double pulse pair is 15-30% lower than the normal motor threshold for the subject.

15. A method according to claim 1 wherein each bi-phasic pulse of the bi-phasic double pulse pair begins at neutral.

* * * * *